(12) United States Patent
Irvin

(10) Patent No.: US 9,671,401 B2
(45) Date of Patent: *Jun. 6, 2017

(54) CALIBRATION SYSTEM FOR USE WITH LATERAL FLOW ASSAY TEST STRIPS

(75) Inventor: Benjamin R. Irvin, Cupertino, CA (US)

(73) Assignee: Polymer Technology Systems, Inc., Indianapolis, IN (US)

(*) Notice: Subject to any disclaimer, the term of this patent is extended or adjusted under 35 U.S.C. 154(b) by 0 days.

This patent is subject to a terminal disclaimer.

(21) Appl. No.: 13/354,949

(22) Filed: Jan. 20, 2012

(65) Prior Publication Data

US 2012/0185198 A1 Jul. 19, 2012

Related U.S. Application Data

(62) Division of application No. 11/175,554, filed on Jul. 5, 2005, now Pat. No. 8,101,415.

(51) Int. Cl.
*G06F 19/00* (2011.01)
*G01N 33/558* (2006.01)

(52) U.S. Cl.
CPC .. *G01N 33/558* (2013.01); *Y10T 436/144444* (2015.01)

(58) Field of Classification Search
CPC ............... Y10T 436/144444; G01N 33/558
USPC ........... 436/80, 95; 422/82.05, 404; 702/104
See application file for complete search history.

(56) References Cited

U.S. PATENT DOCUMENTS

| 5,366,609 | A | 11/1994 | White et al. |
| 5,989,917 | A | 11/1999 | McAleer et al. |
| 6,394,952 | B1 | 5/2002 | Anderson et al. |
| 6,541,266 | B2* | 4/2003 | Modzelewski et al. ........ 436/95 |
| 6,780,645 | B2 | 8/2004 | Hayter et al. |
| 2003/0054567 | A1* | 3/2003 | Miyoshi et al. ............. 436/514 |
| 2003/0175978 | A1 | 9/2003 | Patel |
| 2004/0078149 | A1* | 4/2004 | Matzinger ...................... 702/22 |

FOREIGN PATENT DOCUMENTS

| EP | 1391728 A1 | 2/2004 |
| WO | 9839657 | 9/1998 |
| WO | 99/18426 A1 | 4/1999 |
| WO | 9936777 | 7/1999 |
| WO | 2004/113911 A1 | 12/2004 |

OTHER PUBLICATIONS

Supplementary European Search Report, EP 06786269, dated Jun. 9, 2009.

* cited by examiner

*Primary Examiner* — Rebecca M Fritchman
(74) *Attorney, Agent, or Firm* — Robert P. Ziemian; Haynes and Boone, LLP

(57) ABSTRACT

A method of adjusting a final signal value measured on a lateral flow assay test strip, by: identifying a pre-determined calibration method for the test strip, wherein the pre-determined calibration method corresponds to the manufacturing lot from which the test strip has been made; measuring signal values while performing a lateral flow assay reaction on a test strip; determining a final signal value; and adjusting the final signal value based upon the identified pre-selected calibration method for the test strip.

7 Claims, 3 Drawing Sheets

CALIBRATION SYSTEM FOR USE WITH LATERAL FLOW ASSAY TEST STRIPS

CROSS-REFERENCE TO RELATED APPLICATIONS

The present application is a divisional of U.S. patent application Ser. No. 11/175,554, filed Jul. 5, 2005, the disclosure of which is incorporated herein by reference.

TECHNICAL FIELD

The present invention relates to calibration systems for lateral flow assay test strip measurement systems.

BACKGROUND OF THE INVENTION

A common problem with lateral flow assay test strips is that different test strips tend to produce slightly different results. Unfortunately, no two test strips will perform exactly alike (i.e.: generate identical test result values) even if the test strips have the same amount of reagent embedded therein, and even if they are both exposed to the same amount of analyte. Such discrepancies in lateral flow assay test results may be explained by differences in the physical properties of individual test strips, and also by differences in the fluid flow path along through different test strips. It would instead be desirable to provide a system to reduce, or compensate for, such performance variances among different test strips.

The problem of different test strips exhibiting slightly different test results becomes even more pronounced when the test strips are manufactured from different lots of material. This is due to the fact that different test strip material lots tend to have slightly different physical properties. These material properties influence the spatial distribution of reagents dried therein and, consequently, the efficiency with which they are reconstituted into flowing liquid.

Therefore, it would instead be desirable to provide a system that compensates for performance variances among different test strips both: (a) when the test strips are made from the same lot of material, and (b) when the test strips are made from different lots of material.

SUMMARY OF THE INVENTION

The present invention provides a calibration system that adjusts the final reflectance value measured on a test strip so as to compensate for variations in results that are exhibited among a selection of similar test strips. In one preferred aspect, the calibration system adjusts the final measured reflectance value by comparison to test results exhibited by other test strips that are all from the same manufacturing lot.

In another preferred aspect, the calibration system selects the particular method that is used to perform the adjustment of final reflectance. The selection of the method may involve identifying the pattern of reflectance profiles and associated parameter values uniquely characteristic of a given manufacturing lot of test strips. This system of selecting the particular method to be used for adjusting the final reflectance values of test strips from a particular manufacturing lot is particularly advantageous in that test strips made from different manufacturing lots of material can each be calibrated differently.

In one preferred aspect, the present invention provides a method of adjusting a final signal value measured on a lateral flow assay test strip, by: identifying a pre-determined calibration method for the test strip, wherein the pre-determined calibration method that is selected is characteristic of the manufacturing lot from which the test strip has been made. Signal values are measured while performing a lateral flow assay reaction on a test strip; a final signal value is determined; and the final signal value is then adjusted based upon the identified pre-selected calibration method that is used for the test strip.

For one particular manufacturing lot of test strips, the pre-determined calibration method for the test strip comprises: measuring signal values while performing a lateral flow assay reaction on a test strip; determining a minimum signal value; determining an interim signal value, wherein the interim signal value is measured a pre-determined time period after the minimum signal value is measured; determining a final signal value; and adjusting the final signal value based upon the interim signal value. Optionally, more than one interim signal value may be used, with each of the interim signal values being measured at different times. Optionally as well, the predetermined time period may be zero.

For another particular manufacturing lot of test strips, the pre-determined calibration method for the test strip comprises: measuring signal values while performing a lateral flow assay reaction on a test strip; determining a minimum signal value; determining the time at which the minimum signal value is measured, determining a final signal value; and adjusting the final signal value based upon the minimum signal value and/or the time at which the minimum signal value is measured.

For another particular manufacturing lot of test strips, the pre-determined calibration method for the test strip comprises: measuring signal values while performing a lateral flow assay reaction on a test strip, determining a total signal below a threshold value; determining a final signal value; and adjusting the final signal value based upon the total measured signal below the threshold value.

DETAILED DESCRIPTION OF THE DRAWINGS

Figure 1:
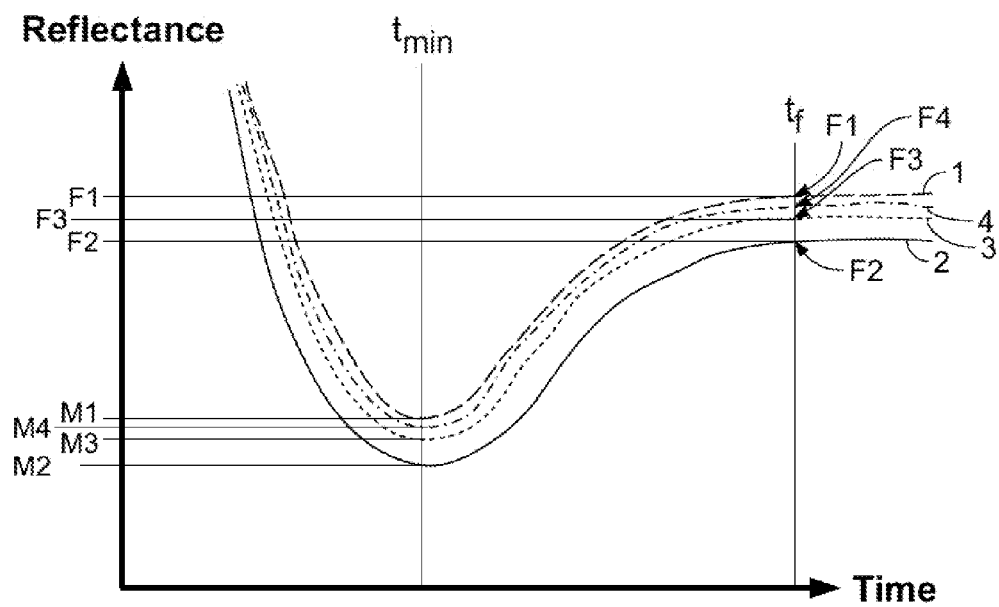
FIG. 1 is an illustration of a pattern of reflectance profiles for a representative sample of lateral flow assay test strips from a first manufacturing lot of material.
Figure 2:
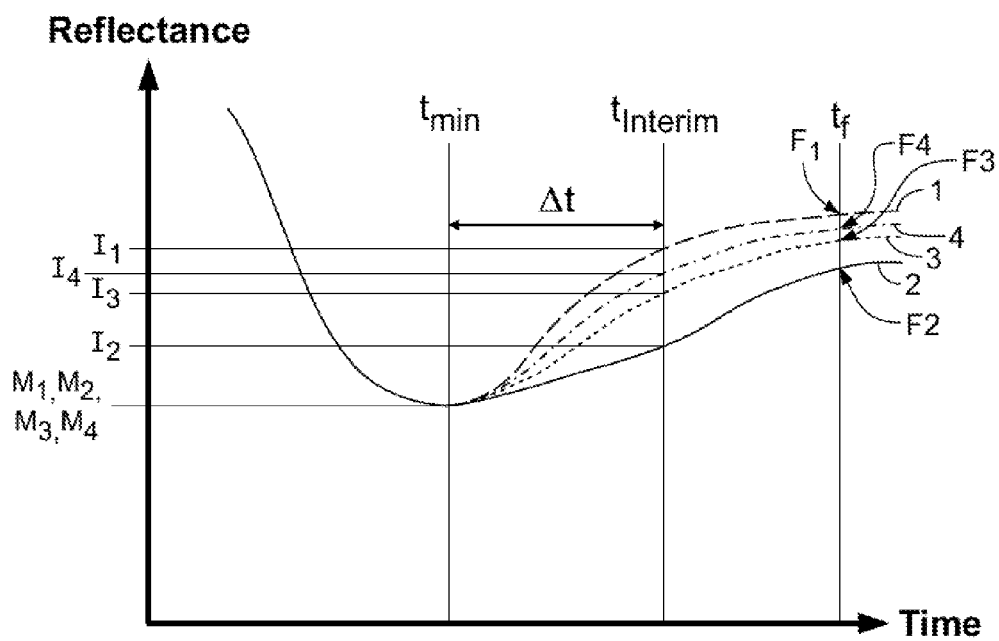
FIG. 2 is an illustration of a pattern of reflectance profiles for a representative sample of lateral flow assay test strips from a second manufacturing lot of material.

FIGS. 1 to 5 each illustrate a representative sample of reflectance profiles for a plurality of lateral flow assay test strips, showing different patterns of kinetics in the test zones of the test strips, wherein: all of the test strips illustrated in FIG. 1 are made from a first manufacturing lot of material; all of the test strips illustrated in FIG. 2 are made from a second manufacturing lot of material, etc.

The examples presented herebelow deal with test strip reflectance profiles. It is to be understood that the present invention is not so limited and that other optical properties including fluorescence or luminescence may be substituted. It is also to be understood that other non-optical properties, including electrochemical signal values and direct light transmission signal values may also instead be used with the present calibration system.

In accordance with the present invention, a specific calibration system is provided for different lots of test strips having the kinetic properties illustrated in each of FIGS. 1 to 5. For example, the test strips from the lot illustrated in FIG. 1 are all calibrated by the one preferred method. Similarly, each of the test strips illustrated in FIG. 2 are all calibrated by another preferred method, and likewise for the test strips illustrated in each of FIGS. 3 to 5. The particular methods of test strip calibration and reflectance value adjustment for each of the test strip manufacturing lots in FIGS. 1 to 5 will be explained fully below.

As stated above, the present invention also provides a system for selecting which specific method of test strip calibration is to be used for any given manufacturing lot of test strips. In accordance with the present invention, a determination is first made as to which kinetic pattern (e.g.: as illustrated in each of FIGS. 1 to 5) is characteristic of the performance of the test strips in a particular manufacturing lot. Then, based on the performance of a representative sample of test strips, the selected manufacturing lot of test strips is calibrated according to the kinetic pattern corresponding to FIG. 1, 2, 3, 4 or 5. For example, for the remaining test strips in the lot, a new test strip may be identified as having the kinetic pattern shown in FIG. 1 (i.e.: the test strip is made from the manufacturing lot of FIG. 1). In this case, the adjustment of final reflectance is made according to the method outlined with respect to FIG. 1. Similarly, if the selected test strip was instead identified as having the kinetic pattern shown in FIG. 2, (i.e.: being made from the manufacturing lot shown in FIG. 2); the calibration of final reflectance is made according to the method outlined with respect to FIG. 2.

FIG. 1 illustrates reflectance kinetic profiles for a plurality of test strips all from a first manufacturing lot. In accordance with the present invention, reflectance profiles are measured for a representative sample of test strips (illustrated here as #1 and #2) under as consistent test conditions as possible. (Such consistent test conditions entail the same amount of reagent in the test strips being exposed to the same amount of analyte in a fluid sample.) From these two extreme reflectance profiles (#1 and #2), a mean, median, expected or "ideal" exemplary test strip reflectance profile (#3) is determined. It is to be understood that reflectance values from more than two representative test strips (#1 and #2) are preferably used to determine the mean test strip reflectance profile #3. Most typically, readings from twenty five or more individual test strips (each falling between the extreme profiles of #1 and #2) are used to determine the mean test strip reflectance profile #3. Thus, it is only for clarity of illustration that only two test strip reflectance profiles (#1 and #2), are shown. Moreover, for clarity of illustration, illustrated reflectance profiles #1 and #2 are the extreme profiles (with each of the other reflectance profiles for the twenty five or more test samples falling therebetween).

As can be seen, the measured reflectance profiles of each of the test strips made from this first lot of material tend to vary from one another with a characteristic pattern, thereby producing a "family" of curves. Specifically, in this particular example, the final reflectance values F will tend to vary in relation to the minimum reflectance values M.

For example, the reflectance of test strip #1 reaches a minimum level $M_1$ at time $t_{min}$, and then reaches its final value $F_1$ at time $t_f$. Similarly, the reflectance of test strip #2 reaches a minimum level $M_2$ after the same elapsed time $t_{min}$, and then reaches its final value $F_2$ at the same elapsed time $t_f$. Since the reflectance profiles of test strips #1 and #2 both reach their minimum levels $M_1$ and $M_2$ at about the same time $t_{min}$, the mean reflectance profile of a nominal (i.e.: newly selected) test strip #3 will also reach its minimum level $M_3$ at time $t_{min}$.

As can also be seen, for test strip #1, the difference between its final reflectance value $F_1$ and the average or expected final reflectance value $F_3$ will vary in relation to the difference between the minimum reflectance value $M_1$ and the mean minimum reflectance value $M_3$. In certain exemplary cases, this relationship may be linear, but the present invention is not so limited.

Similarly, for test strip #2, the difference between its final reflectance value $F_2$ and the average final reflectance value $F_3$ will vary in relation to the difference between the minimum reflectance value $M_2$ and the mean minimum reflectance value $M_3$. In certain exemplary cases, this relationship may be linear, but again the present invention is not so limited. A calibration equation with associated parameter values may thus be defined for the manufacturing lot illustrated in FIG. 1.

Therefore, variability in additional (i.e.: newly selected) test strips, made from the same manufacturing lot shown in FIG. 1, may be mitigated by adjustment using the calibration information established as above for this exemplary manufacturing lot of test strips, as follows. The reflectance profile of an additional (i.e.: newly selected or "nominal") test strip #4 is illustrated. Variation in the final reflectance value of test strip #4 can be mitigated by simply measuring its minimum reflectance value $M_4$, at time $t_{min}$, and adjusting its final reflectance value $F_4$ downwardly (from $F_4$ to $F_3$) by an amount proportional to the difference between $M_4$ and $M_3$ according to the calibration equation established for this exemplary manufacturing lot of test strips. Note: if the minimum reflectance value of test strip #4 does not occur near $t_{min}$, an error message may be triggered.

FIG. 2 illustrates reflectance kinetic profiles for a plurality of test strips from a second manufacturing lot of material. In accordance with the present invention, reflectance profiles are measured for a representative sample of test strips (illustrated here as #1 and #2) under as consistent test conditions as possible. (As above, consistent test conditions entail the same amount of reagent in the test strips being exposed to the same amount of analyte in a fluid sample.) From these two extreme reflectance profiles (#1 and #2), a mean, median, expected or "ideal" exemplary test strip reflectance profile (#3) is determined. It is to be understood that reflectance profiles from more than two representative test strips (#1 and #2) are preferably used to determine the mean test strip reflectance profile #3. Most typically, readings from twenty five or more individual test strips (each falling between the extreme profiles of #1 and #2) are used to determine average test strip reflectance value #3. Thus, it is only for clarity of illustration that only two test strip reflectance values (#1 and #2), are shown. Reflectance profile #3 thus represents a mean, or standard or expected reflectance profile for a test strip that is made from the lot of material shown in FIG. 2. Moreover, for clarity of illustration, illustrated reflectance profiles #1 and #2 are the extreme profiles (with each of the other reflectance profiles for the twenty five or more test samples falling therebetween).

As can be seen, the measured reflectance profiles of each of the test strips made from this second lot of material tend to vary in the same way from one another, within a characteristic pattern, thereby producing a "family" of curves. Specifically, in this particular example, the final reflectance values F will tend to vary in relation to an interim reflectance value I, with the minimum reflectance values, $t_n$, all being essentially identical and all occurring at essentially the same time $t_{min}$.

For example, the reflectances of test strips #1 and #2 both reach the same minimum level (i.e. $M_1 = M_2$) at about the same time $t_{min}$. Therefore, the reflectance of mean test strip #3 will also reach its minimum level $M_3$ at about time $t_{min}$. The reflectance of test strip #1 then reaches its final value $F_1$ at time $T_f$, and the reflectance of test strip #2 also reaches its final value $F_2$ at time $t_f$. As can be seen, the measured reflectances of test strips #1 and #2 will tend to vary most from one another when measured at an interim time period $t_{interim}$. Further, $t_{interim}$ occurs at a time delay "$\Delta t$" after $t_{min}$ (i.e. at a time delay $\Delta t$ after the measurement of minimum reflectances $M_1$ and $M_2$).

In the case of the measured test strip reflectance in the reflectance profile shown by test strip #1, the difference between the final reflectance value $F_1$ and the average final reflectance value $F_3$ will vary in relation to the difference between the reflectance values $I_1$ and $I_3$ measured a predetermined time delay "$\Delta t$" after $t_{min}$ (i.e. at a time delay $\Delta t$ after the minimum reflectance $M_1$ is measured). For example, the difference between the final reflectance value $F_1$ and the average final reflectance value $F_3$ is directly proportional to the difference between the reflectance value measured at time $t_{interim}$ between $I_2$ and $I_3$. In certain exemplary cases, this relationship may be linear, but the present invention is not so limited.

Similarly, in the case of the measured test strip reflectance profile shown by test strip #2, the difference between the final reflectance value $F_2$ and the mean final reflectance value $F_3$ will vary in relation to the difference between the reflectance values $I_2$ and $I_3$ measured a pre-determined time delay "$\Delta t$" after $t_{min}$ (i.e. at a time delay $\Delta t$ after the minimum reflectance $M_2$ is measured). For example, the difference between the final reflectance value $F_2$ and the average final reflectance value $F_3$ is directly proportional to the difference between the reflectance values $I_2$ and $I_3$ measured at time $t_{interim}$ between $F_2$ and $F_3$. In certain exemplary cases, this relationship may be linear, but the present invention is not so limited. As above, a calibration equation with associated parameter values may thus be defined for the manufacturing lot illustrated in FIG. 2.

Therefore, variability in additional (i.e.: newly selected) test strips made from the same manufacturing lot shown in FIG. 2, may be mitigated by adjustment using the calibration information established as above for this exemplary manufacturing lot of test strips, as follows. The reflectance profile of an additional (i.e.: newly selected) test strip #4 is illustrated. Variation in the final reflectance value of test strip #4 can be mitigated by simply measuring its interim reflectance value $I_4$, and adjusting its final reflectance value $F_4$ downwardly (from $F_4$ to $F_3$) by an amount proportional to the difference between $I_4$ and $I_3$ according to the calibration equation established for this exemplary manufacturing lot of test strips.

Figure 3:
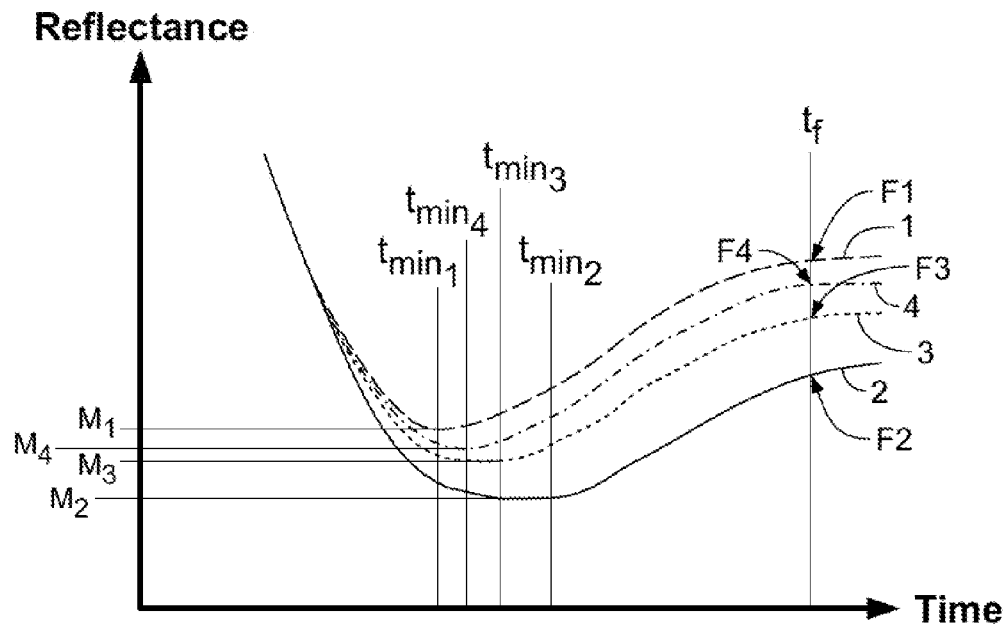
FIG. 3 is an illustration of a pattern of reflectance profiles for a representative sample of lateral flow assay test strips from a third lot of manufacturing material.

FIG. 3 illustrates reflectance kinetic profiles for a plurality of test strips from a third manufacturing lot. In accordance with the present invention, reflectance profiles are measured for a representative sample of test strips (illustrated as #1 and #2). From these two reflectance profiles (#1 and #2), a mean, median, expected or "ideal" exemplary test strip reflectance profile (#3) is generated for the third lot of material. It is to be understood that reflectance profiles from more than two representative test strips are preferably used to generate a mean test strip reflectance profile #3. Most typically, readings from twenty five or more individual test strips (each falling between the illustrated extreme profiles of #1 and #2) are used to generate mean test strip reflectance profile #3. Thus, it is only for clarity of illustration that only two test strip reflectance profiles (#1 and #2), are shown.

As can be seen, the measured reflectance profiles of each of the test strips from this third lot of material tend to vary within a characteristic pattern, thereby producing a "family" of curves. More specifically, in this particular example, the final reflectance values F will tend to vary in relation to the time at which the minimum reflectance value $t_{min}$ is measured.

For example, the reflectance of test strip #1 reaches a minimum level $M_1$ at time $t_{min1}$, and then reaches its final value $F_1$ at time $t_f$. Similarly, the reflectance of test strip #2 reaches its minimum level $M_2$ at its own particular time $t_{min2}$. As can be seen, the reflectance of average test strip #3 will therefore also reach its minimum level $M_3$ at its own time $t_{min3}$. As can be seen, the difference between the final reflectance value $F_1$ or $F_2$ and the average final reflectance value $F_3$ is a function of the time at which $t_{min1}$ or $t_{min2}$ is reached.

Thus, in the case of test strips from the third lot (i.e.: the lot measured in FIG. 3) the final reflectance values can accurately be adjusted by simply determining when the minimum reflectance values are measured and applying the appropriate lot-specific calibration equation and associated parameter values.

Therefore, variability in additional (i.e.: newly selected) test strips from the same manufacturing lot shown in FIG. 3, may be mitigated by adjustment using the calibration information established as above for this exemplary manufacturing lot of test strips, as follows. The reflectance profile of an additional (i.e.: newly selected) test strip #4 is illustrated. Variation in the final reflectance value of test strip #4 can be mitigated by simply measuring the time $t_{min4}$ at which it reaches its minimum reflectance value $M_4$. As such, the final reflectance value $F_4$ will be adjusted downwardly (from $F_4$ to $F_3$) by an amount proportional to the time difference between $t_{min4}$ and $t_{min3}$ according to the calibration equation established for this exemplary manufacturing lot of test strips.

Figure 4:
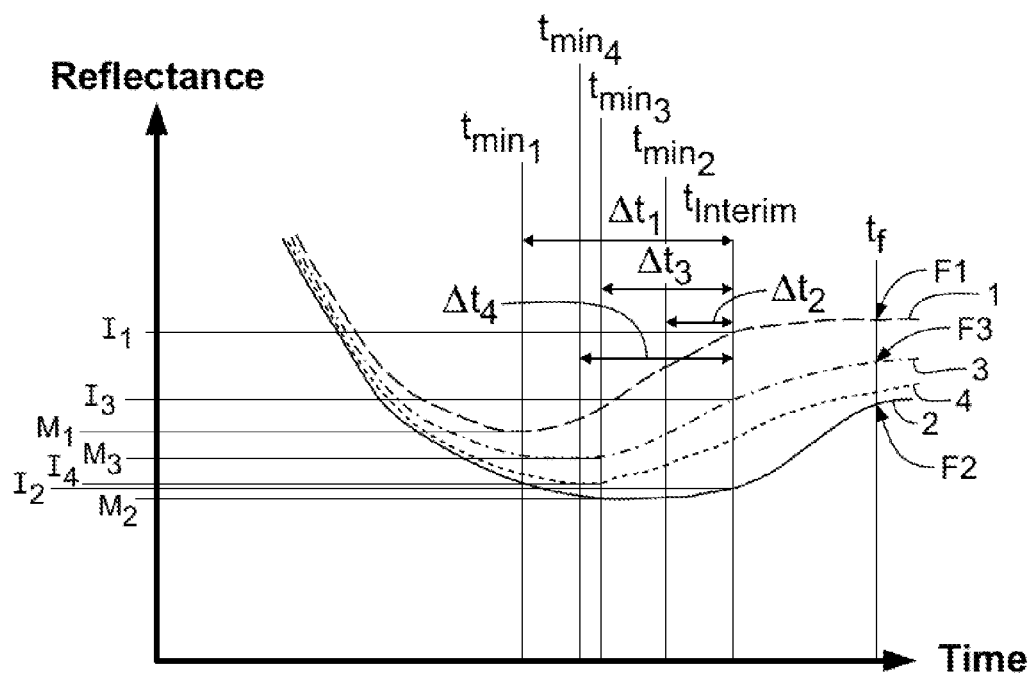
FIG. 4 is an illustration of a pattern of reflectance profiles for a representative sample of lateral flow assay test strips from a fourth lot of manufacturing material.

FIG. 4 illustrates reflectance kinetic profiles for a plurality of test strips from a fourth manufacturing lot. In accordance with the present invention, reflectance profiles are measured for a representative sample of test strips (illustrated as #1 and #2). From these two reflectance profiles (#1 and #2), a mean test strip reflectance profile (#3) is generated. It is to be understood that reflectance profiles from more than two representative test strips are preferably used to generate an average test strip reflectance profile #3. Thus, it is only for clarity of illustration that only two test strip reflectance profiles (#1 and #2), are shown. Moreover, for clarity of illustration, illustrated reflectance profiles #1 and #2 are the extreme profiles (with each of the other reflectance profiles for the twenty five or more test samples falling therebetween).

As can be seen, the measured results of each of the test strips from this fourth lot of material tend to vary within a characteristic pattern, thereby producing a "family" of curves. More specifically, in this particular example, the final reflectance values F will tend to vary in relation to both the minimum reflectance values and the time at which these minimum reflectance values are measured.

For example, the reflectance of test strip #1 reaches a minimum level $M_1$ at time $t_{min1}$ and then reaches its final value $F_1$ at time $t_f$. Similarly, the reflectance of test strip #2 reaches its own minimum level $M_2$ at its own time $t_{min2}$. Therefore, the reflectance of average test strip #3 will reach its minimum level $M_3$ at its own time $t_{min3}$.

As can also be seen, the measured reflectances of test strips #1 and #2 will tend to vary most from one another when measured at an interim time period $t_{interim}$. Further, $t_{interim}$ occurs at various time delays $\Delta t_n$ after $t_{min}$.

For example, $I_1$ occurs at $t_{interim}$ (where $t_{interim}$ is measured at time delay $\Delta t_1$ after minimum value $M_1$ has been measured). Similarly, $I_2$ occurs at $t_{interim}$ (where $t_{interim}$ is measured at time delay $\Delta t_2$ after minimum value $M_2$ has been measured). Therefore, $I_3$ will occur at $t_{interim}$ (where $t_{interim}$ is measured at time delay $\Delta t_3$ after minimum value $M_3$ has been measured).

Therefore, variability in additional (i.e.: newly selected) test strips from the same manufacturing lot shown in FIG. 4, may be mitigated by adjustment using the calibration information established as above for this exemplary manufacturing lot of test strips, as follows. The reflectance profile of an additional (i.e.: newly added) test strip #4 is illustrated. Variation in final reflectance value in test strip #4 can be mitigated by adjusting the final reflectance value $F_4$ by simply determining both the minimum reflectance values, and the time at which the minimum reflectance values are measured, as follows.

For example, test strip #4 will be calibrated by first measuring the interim value $I_4$ at time $t_{interim}$ (measured at delay $\Delta t_4$ after it reaches its minimum reflectance value $M_4$). The length of delay $\Delta t_4$ is determined by the time $t_{min4}$ at which $M_4$ is measured. As such, the final reflectance value $F_4$ will be adjusted upwardly (from $F_4$ to $F_3$) by an amount proportional to the difference between interim reflectance values $I_4$ and $I_3$ according to the calibration equation established for this exemplary manufacturing lot of test strips.

In summary, each of FIGS. 1 to 4 illustrate different patterns of reflectance kinetics, each being characteristic of a particular manufacturing lot of test strips. In the case of the lot shown in FIG. 1, adjustment of the final reflectance value F is made solely by comparing minimum test values M. In the case of the lot shown in FIG. 2, adjustment of the final reflectance value F is made solely by comparing interim reflectance values I (wherein the interim value I is measured a pre-determined time period $\Delta t$ after the minimum value M is detected). In the case of the lot shown in FIG. 3, adjustment of the final reflectance value F is made solely by comparing the time $t_{min}$ at which the minimum test value M is detected. Lastly, in the case of the lot shown in FIG. 4, adjustment of the final reflectance value F is made by comparing both the minimum test values M and the times $t_{min}$ at which these minimum test values M are detected.

It is to be understood that the exemplary aspects of the preferred calibration illustrated in FIGS. 1 to 4 are exemplary, and are not limiting. For example, other suitable techniques may be used to generate or determine the exemplary mean reflectance profile (e.g.: reflectance profile #3) of an exemplary or nominal test strip from a particular manufacturing lot.

Therefore, any suitable technique for determining an exemplary reflectance profile (e.g.: reflectance profile #3) of a mean test strip made from a particular manufacturing lot of material is encompassed within the scope of the present invention. Thus, calibration systems including curve-fitting techniques, and techniques where measurements are made at a number of different interim test points for each test strip, are all encompassed within the scope of the present invention. The values taken at each of these different interim test points may be weighted equally, or they may be weighted differently from one another in computing the "ideal" or exemplary typical test strip reflectance profile #3 that is best representative for the particular manufacturing lot of test strips. In addition, systems that exhibit reflectance profile #3 and use medians instead of means are also encompassed within the scope of the present invention. Such an approach may be advantageous in that calculating medians tends to be more effective in reducing the effects of outliers. Optionally, methods that take into account rates of reflectance changes over time may also be used in calculating "ideal" or representative exemplary test strip reflectance profiles #3.

Figure 5:
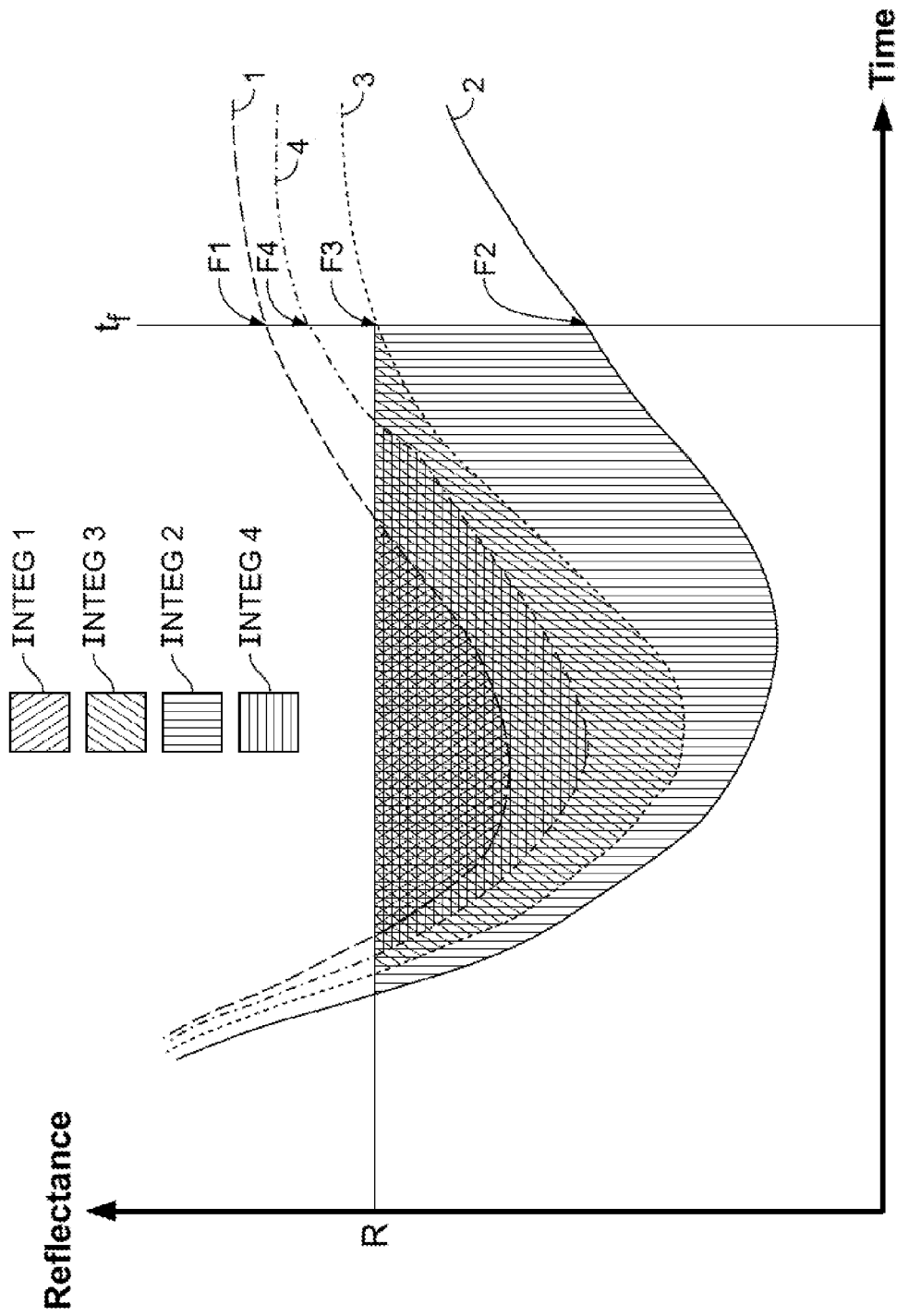
FIG. 5 is an illustration of a pattern of reflectance profiles for a representative sample of lateral flow assay test strips from a fifth lot of manufacturing material.

FIG. 5 illustrates reflectance kinetic profiles for a plurality of test strips from a fifth manufacturing lot. In accordance with the present invention, reflectance profiles are measured for a representative sample of test strips (illustrated as #1 and #2). The final reflectance value $F_1$ at time $t_f$ for test strip #1 is determined. Then, the area (i.e.: the "total signal") below a given reflectance value R and above line #1 is determined. (See shaded area labeled INTEG 1.) Similarly, the final reflectance value $F_2$ at time $t_f$ for test strip #2 is determined. Then, the area (i.e.: the "total signal") below final reflectance value R and above line #2 is determined. (See shaded area labeled INTEG 2.)

From these two reflectance total signals (INTEG1 and INTEG 2), an average test strip reflectance total signal (INTEG3) is generated for the lot of test strips illustrated in FIG. 5. It is to be understood that reflectance profiles from more than two representative test strips are preferably used to generate an average test strip reflectance profile #3. Thus, it is only for clarity of illustration that only two test strip reflectance profiles (#1 and #2), are shown. Note: in the example shown in FIG. 5, the reflectance value R is the same as the final reflectance value $F_3$. This need not be true in all cases. Instead, other threshold reflectance values R may be used in accordance with the calibration method illustrated in FIG. 5. Similar to the above described Figs, reflectance profiles #1 and #2 are illustrated as extreme values.

In accordance with one aspect of the invention, the final reflectance value $F_3$ at time $t_f$ for an average or ideal test strip #3 is determined. In addition, the area (i.e.: "total signal") below final reflectance value $F_3$ and above line #3 is also determined. (See shaded area labeled INTEG 3.)

Therefore, in the case of newly selected test strips from the fifth lot (i.e.: the lot measured in FIG. 5) the final reflectance values can accurately be adjusted by simply determining the total signal under reflectance value R for the particular newly selected test strip and applying the appropriate lot-specific calibration equation and associated parameter values.

For example, in the case of a new test strip #4 made from the manufacturing lot shown in FIG. 5, test strip #4 can be adjusted by simply measuring the area INTEG 4 and comparing the area of INTEG 4 to the area of average test strip INTEG 3. As such, the final reflectance value $F_4$ will be adjusted downwardly (from $F_4$ to $F_3$) by an amount proportional to the difference in size between INTEG 4 and INTEG 3 according to the calibration equation established for this exemplary manufacturing lot of test strips.

As understood herein, a lateral flow assay test strip encompasses any quantitative lateral flow assay system that is based on the capture of a signal generating species as it flows through a detection zone. In preferred embodiments, the reflectance values may be measured at a location on the test strip as a sample with a concentrated front of dyed microparticles passes thereover, and wherein the final reflectance value is measured at the location on the test strip after microparticle capture and clearing of non-bound microparticles has occurred. Preferably, the signal values are all measured at the same location on the test strip.

Any of the above final signal values F may be measured a pre-determined period of time after the commencement of the lateral flow assay reaction.

In accordance with the present invention, minimum signal values may be used when analyzing reflectance kinetic profiles. In contrast, maximum signal values may be used when examining fluorescence kinetic profiles. Therefore, in the present specification and claims, the term "maximum" may be substituted for the term "minimum". Moreover in the present specification and claims, the term "extreme" may be used to include either a "maximum" or a "minimum". As also understood herein, an "exemplary" test strip (i.e.: #3 as illustrated herein) may include a calculated mean, median or average test strip that is representative of test strips from a particular manufacturing lot.

Also in accordance with the present invention is identifying the pre-determined calibration method used for the manufacturing lot, to which a particular newly selected test strip belongs, by reading an identifier that indicates which pre-determined adjustment method is to be used. For example, a test strip made from the manufacturing lot of test strips shown in FIG. 1 may carry an identification tag stating that the calibration method to be used is that which is illustrated in FIG. 1, along with the parameter values uniquely characteristic of that test strip's manufacturing lot, wherein such an identification tag may be mounted on the test strip itself or on an assembly connected to the test strip.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A method of adjusting a final signal value measured on a lateral flow assay test strip, comprising:
measuring signal values, the signal values resulting from optical analysis of a test strip with a meter wherein the meter measures the signal values, while performing a lateral flow assay reaction on the test strip, each of the signal values representative of an optical property of the lateral flow assay test strip at a point in time, the signal values measured over a time period during which the lateral flow assay test strip is tested;
determining a minimum signal value using the meter, the meter configured to perform the determining of the minimum signal value and including instructions that the meter executes, the instructions stored in a computer readable medium, wherein the minimum signal value is the minimum measured value of reflectance measurements of the signal values;
determining the time at which the minimum signal value is measured;
determining a final signal value, wherein the minimum signal value and the final signal value are not the same using the meter, the meter configured to perform the determining of the time and the final signal value and including instructions that the meter executes, the instructions stored in a computer readable medium; and
adjusting the final signal value using the meter to account for differences in a lot of test strips from which the lateral flow assay test strip originates as compared to an expected test strip, the lot of test strips from the same manufacturing lot, the meter configured to perform the adjusting of the final signal and including instructions that the meter executes, the instructions stored in a computer readable medium, based upon the time at which the minimum signal value is measured compared to an expected time at which minimum signal values are reached, wherein the final signal value is decreased when the minimum signal value is measured early as compared to the expected time.

2. A method of adjusting a final signal value measured on a lateral flow assay test strip, comprising:
measuring signal values, the signal values resulting from optical analysis of a test strip with a meter wherein the meter measures the signal values, while performing a lateral flow assay reaction on the test strip, each of the signal values representative of an optical property of the lateral flow assay test strip at a point in time, the signal values measured over a time period for testing the test strip;
determining a total signal below a threshold value using the meter, the meter configured to perform the determining of the total signal below a threshold value and including instructions that the meter executes, the instructions stored in a computer readable medium, wherein the total signal below the threshold value is based on a total area calculated between a line formed by the signal values and the threshold value;
determining a final signal value; and
adjusting the final signal value using the meter to account for differences in a lot of test strips from which the lateral flow assay test strip originates as compared to an expected test strip, the lot of test strips from the same manufacturing lot, the meter configured to perform the adjusting of the final signal and including instructions that the meter executes, the instructions stored in a computer readable medium, based upon comparing the total measured signal below the threshold value, which is a graphed area between the threshold value and a curve composed of the signal values, to an expected total measured signal, wherein the final signal value is increased when the graphed area is less than the expected total measured signal.

3. The method of claim 2, wherein the signal values are reflectance values.

4. A method of adjusting a final signal value measured on a lateral flow assay test strip, comprising:
measuring signal values, the signal values resulting from optical analysis of a test strip with a meter wherein the meter measures the signal values, while performing a lateral flow assay reaction on the test strip, each of the signal values representative of an optical property of the lateral flow assay test strip at a point in time, the signal values measured over a time period during which the lateral flow assay test strip is tested;
determining a minimum signal value using the meter, the meter configured to perform the determining of the minimum signal value and including instructions that the meter executes, the instructions stored in a computer readable medium, wherein the minimum signal value is the minimum measured value of reflectance measurements of the signal values;

determining the time at which the minimum signal value is measured;

determining a final signal value, wherein the minimum signal value and the final signal value are not the same using the meter, the meter configured to perform the determining of the time and the final signal value and including instructions that the meter executes, the instructions stored in a computer readable medium; and adjusting the final signal value using the meter to account for differences in a lot of test strips from which the lateral flow assay test strip originates as compared to an expected test strip, the lot of test strips from the same manufacturing lot, the meter configured to perform the adjusting of the final signal and including instructions that the meter executes, the instructions stored in a computer readable medium, based upon the time at which the minimum signal value is measured compared to an expected time at which minimum signal values are reached, wherein the final signal value is increased when the minimum signal value is measured late as compared to the expected time.

5. The method of claim 1, wherein the amount of decrease of the final signal value is proportional to a difference between the time at which the minimum signal value is measured and the expected time.

6. The method of claim 4, wherein the amount of increase of the final signal value is proportional to a difference between the time at which the minimum signal value is measured and the expected time.

7. A method of adjusting a final signal value measured on a lateral flow assay test strip, comprising:

measuring signal values, the signal values resulting from optical analysis of a test strip with a meter wherein the meter measures the signal values, while performing a lateral flow assay reaction on the test strip, each of the signal values representative of an optical property of the lateral flow assay test strip at a point in time, the signal values measured over a time period for testing the test strip;

determining a total signal below a threshold value using the meter, the meter configured to perform the determining of the total signal below a threshold value and including instructions that the meter executes, the instructions stored in a computer readable medium, wherein the total signal below the threshold value is based on a total area calculated between a line formed by the signal values and the threshold value;

determining a final signal value; and adjusting the final signal value using the meter to account for differences in a lot of test strips from which the lateral flow assay test strip originates as compared to an expected test strip, the lot of test strips from the same manufacturing lot, the meter configured to perform the adjusting of the final signal and including instructions that the meter executes, the instructions stored in a computer readable medium, based upon comparing the total measured signal below the threshold value, which is a graphed area between the threshold value and a curve composed of the signal values, to an expected total measured signal, wherein the final signal value is decreased when the graphed area is greater than the expected total measured signal.

\* \* \* \* \*